(12) United States Patent
Satou et al.

(10) Patent No.: US 8,273,805 B2
(45) Date of Patent: Sep. 25, 2012

(54) INK-JET INK

(75) Inventors: Hiroyuki Satou, Chiba (JP); Setsuo Itami, Chiba (JP); Yosihiro Deyama, Chiba (JP)

(73) Assignee: JNC Corporation, Tokyo (JP)

( * ) Notice: Subject to any disclaimer, the term of this patent is extended or adjusted under 35 U.S.C. 154(b) by 873 days.

(21) Appl. No.: 12/021,921

(22) Filed: Jan. 29, 2008

(65) Prior Publication Data

US 2008/0182086 A1    Jul. 31, 2008

(30) Foreign Application Priority Data

Jan. 31, 2007 (JP) .................................. 2007-20673

(51) Int. Cl.
*C09D 11/00* (2006.01)
(52) U.S. Cl. ........ 523/160; 522/171; 523/161; 524/547; 524/548; 524/556; 524/558; 526/266; 526/274; 526/275; 526/319; 526/320; 526/332; 549/216; 549/217
(58) Field of Classification Search .................. 523/160, 523/161; 524/556, 558, 547, 548; 526/275, 526/320, 266, 274, 319, 332; 522/171; 549/216, 549/217
See application file for complete search history.

(56) References Cited

U.S. PATENT DOCUMENTS

| | | | |
|---|---|---|---|
| 2002/0022117 A1* | 2/2002 | Kitamura et al. | ............ 428/195 |
| 2003/0134926 A1* | 7/2003 | Fukada et al. | .................. 522/81 |
| 2005/0282938 A1* | 12/2005 | Yamaguchi et al. | .......... 523/513 |
| 2006/0183824 A1* | 8/2006 | Hosaka et al. | .................. 524/99 |

FOREIGN PATENT DOCUMENTS

| | | |
|---|---|---|
| JP | 2003302642 | 10/2003 |
| JP | 2006282757 | 10/2006 |
| JP | 2006307152 | 11/2006 |
| WO | 2004099272 | 11/2004 |

* cited by examiner

*Primary Examiner* — David W Wu
*Assistant Examiner* — Marie Reddick
(74) *Attorney, Agent, or Firm* — J.C. Patents

(57) ABSTRACT

An ink-jet ink is provided. The ink-jet ink includes a compound of formula (1) to form a cured film with high-flame retardancy. In the formula, R is hydrogen, hydroxyl, or an organic group of 1 to 100 carbon atoms; and n is an integer of 1 to 20:

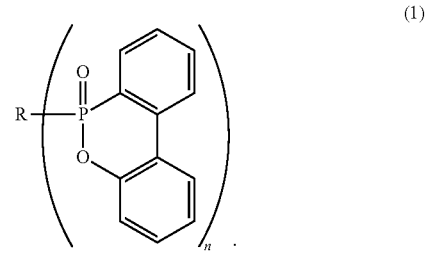

(1)

22 Claims, No Drawings

INK-JET INK

CROSS-REFERENCE TO RELATED APPLICATION

This application claims the priority benefit of Japan application serial no. 2007-20673, filed on Jan. 31, 2007. The entirety of the above-mentioned patent application is hereby incorporated by reference herein and made a part of this specification.

BACKGROUND OF THE INVENTION

1. Field of the Invention

The invention generally relates to an ink-jet ink. More particularly, the invention relates to an ink-jet ink applicable for manufacturing liquid crystal display (LCD) elements, electroluminance display elements, printed circuit boards (PCBs), and so on. Furthermore, the invention relates to a method of forming a cured film by using an ink-jet ink and an electronic circuit substrate with a cured film formed thereon.

2. Description of Related Art

Generally, in order to ensure safety, electronic circuit substrates are required to use flame-retardant materials. In recent years, as for a method of forming a patterned cured film when manufacturing an electronic circuit substrate, the ink-jet printing process having the advantages of lower capital investment on equipments and higher material-use efficiency has been proposed, and a composition (an ink-jet ink) used in the method has also been proposed (for example, Japanese Patent Publication No. 2003-302642, WO 2004/099272, Japanese Patent Publication No. 2006-282757, Japanese Patent Publication No. 2006-307152).

However, the cured filmed formed by these ink-jet inks do not have sufficient flame retardancy.

SUMMARY OF THE INVENTION

Accordingly, the invention is directed to an ink-jet ink capable of forming a high flame-retardant cured film.

The inventors found that, a cured film formed by an ink-jet ink containing a compound of a special structure can achieve a high flame retardancy, and thus the invention is completed based upon this discovery.

As embodied and broadly described herein, the invention provides an ink-jet ink as follows.

1. An ink-jet ink comprising a compound (A) of a formula (1):

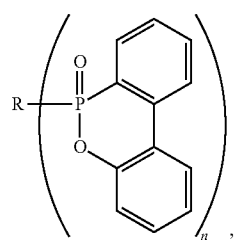

wherein R is hydrogen, hydroxyl, or an organic group of 1 to 100 carbon atoms, and n is an integer of 1 to 20, is provided.

2. The ink-jet ink according to Item 1, wherein R is hydrogen, hydroxyl, or an organic group of 1 to 70 carbon atoms, and n is an integer of 1 to 15.

3. The ink-jet ink according to Item 1, wherein R is hydrogen, hydroxyl, or an organic group of 1 to 40 carbon atoms, and n is an integer of 1 to 10.

4. The ink-jet ink according to any one of Items 1 to 3, wherein R has a double bond.

5. The ink-jet ink according to Item 4, wherein the double bond is a radical polymerizable double bond.

6. The ink-jet ink according to any one of Items 1 to 5, wherein R has a hydroxyl.

7. The ink-jet ink according to any one of Items 1 to 6, wherein R has an oxiranyl group.

8. The ink-jet ink according to any one of Items 1 to 7, wherein R has an oxetanyl group.

9. The ink-jet ink according to any one of Items 1 to 8, wherein R has a carboxyl group.

10. The ink-jet ink according to any one of Items 1 to 9, wherein R has an amino group.

11. The ink-jet ink according to any one of Items 1 to 10, wherein the ink-jet ink further comprises a polymerizable monomer (B).

12. The ink-jet ink according to Item 11, wherein the polymerizable monomer (B) has a hydroxyl.

13. The ink-jet ink according to Item 12, wherein the polymerizable monomer (B) comprises a monofunctional monomer with a hydroxyl.

14. The ink-jet ink according to Item 13, wherein the polymerizable monomer (B) is a compound of formula (2):

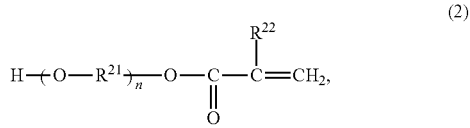

wherein $R^{21}$ is alkylene having 2 to 12 carbon atoms may have a ring structure, $R^{22}$ is alkyl of 1 to 3 carbon atoms or hydrogen, and n is an integer of 1 to 30.

15. The ink-jet ink according to Item 14, wherein $R^{21}$ is alkylene having 2 to 12 carbon atoms may have a ring structure, $R^2$ is methyl or hydrogen, and n is an integer of 1 to 10.

16. The ink-jet ink according to Item 14, wherein $R^{21}$ is alkylene having 2 to 12 carbon atoms may have a ring structure, $R^2$ is methyl or hydrogen, and n is integer of 1 to 5.

17. The ink-jet ink according to Item 13, wherein the polymerizable monomer (B) includes a multifunctional polymerizable monomer and a monofunctional monomer having a hydroxyl.

18. The ink-jet ink according to any one of Items 1 to 17 further contains a photo-polymerization initiator (C).

19. The ink-jet ink according to Item 18, wherein the photo-polymerization initiator (C) is a compound of formula (3) or (4), wherein $R^1$-$R^{15}$ are independently hydrogen, alkyl of 1 to 5 carbon atoms, or phenyl with or without a substituted group:

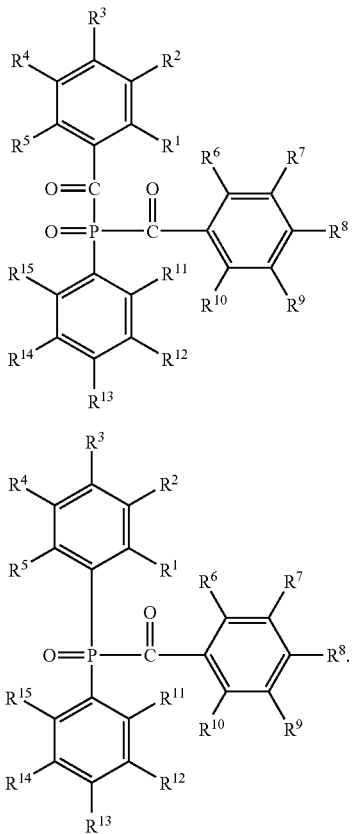

20. The ink-jet ink according to Item 19, wherein the photo-polymerization initiator (C) is one of bis(2,4,6-trimethylbenzoyl)phenyl phosphine oxide of formula (3) with $R^1$, $R^3$, $R^5$, $R^6$, $R^8$, and $R^{10}$ as methyl and $R^2$, $R^4$, $R^7$, $R^9$, $R^{11}$, $R^{12}$, $R^{13}$, $R^{14}$, and $R^{15}$ as hydrogen and (2,4,6-trimethylbenzoyl)diphenyl phosphine oxide of formula (4) with $R^6$, $R^8$, and $R^{10}$ as methyl and $R^1$, $R^2$, $R^3$, $R^4$, $R^5$, $R^7$, $R^9$, $R^{11}$, $R^{12}$, $R^{13}$, $R^{14}$ and $R^{15}$ as hydrogen.

21. An ink-jet ink comprises a compound (A), having a structure of formula (5); a polymerizable monomer (B), being one or more selected from a group consisting of 2-hydroxyethyl(meth)acrylate, 2-hydroxypropyl(meth)acrylate, 4-hydroxybutyl (meth)acrylate, and 1,4-cyclohexanedimethanol mono(meth)acrylate; and a photo-polymerization initiator (C), being one or more selected from a group consisting of bis(2,4,6-trimethylbenzoyl)phenyl phosphine oxide and (2,4,6-trimethylbenzoyl)diphenyl phosphine oxide,

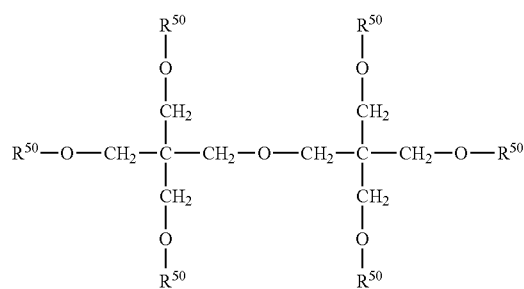

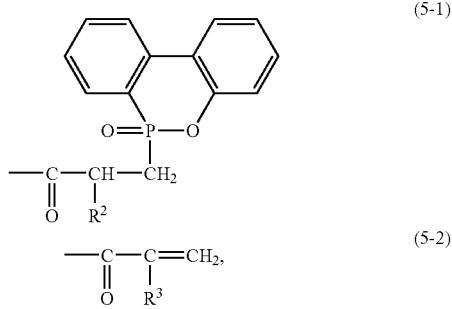

wherein $R^{50}$ includes n formulae (5-1), m formulae (5-2), n is an integer of 1 to 5, m is an integer of 1 to 5, and n+m is 6; $R^2$ is hydrogen or methyl, and $R^3$ is hydrogen or methyl is provided.

22. A method of forming a cured film including firstly coating the ink-jet ink according to any one of Items 1 to 21 by an ink jet printing process, and then irradiating by lights, so as to form the cured film is provided.

23. An electronic circuit substrate in which a flame-retardant cured film is formed on the substrate through the method of forming the cured film according to Item 22 is provided.

24. An electronic component having the electronic circuit substrate according to Item 23 is provided.

25. A display element having a cured film formed through the method of forming the cured film according to Item 22 is provided.

Furthermore, in this specification, (meth)acrylate represents both acrylates and methacrylates.

In an embodiment of the invention, as the cured film formed by using the ink-jet ink has a high flame retardancy, it can be safely used as a material for an electronic circuit substrate.

BRIEF DESCRIPTION OF THE DRAWINGS

No Drawings.

DESCRIPTION OF THE EMBODIMENTS

Reference will now be made in detail to the embodiments of the invention, examples of which are illustrated in the accompanying drawings. Wherever possible, the same reference numbers are used in the drawings and the description to refer to the same or like parts.

1. Ink-Jet Ink of the Invention

The ink-jet ink of the invention at least contains a compound (A) of formula (1).

As long as the compound (A) of formula (1) is contained, the ink-jet ink of the invention is not specially limited, which may be further obtained by mixing or dissolving a polymerizable monomer (B), and photo-polymerization initiator (C), and so on.

1.1 Compound (A) of Formula (1)

The ink-jet ink of the invention preferably contains the compound (A) of formula (1), that is because the cured film formed by the ink-jet of the invention has a high-flame retardancy. The content of the compound (A) of formula (1) is preferably greater than or equal to 10 wt %, based on the total weight except the ink-jet ink solvent, and thus the flame retardancy is relatively high. Considering the balance of other properties, the content of the compound (A) of formula (1) is preferably 10 wt %-70 wt %:

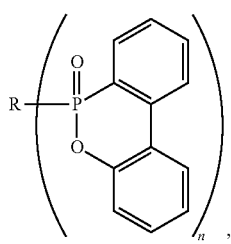
(1)

wherein R is hydrogen, hydroxyl, or an organic group of 1 to 100 carbon atoms, and n is an integer of 1 to 20.

As for the compound (A) of formula (1), preferably, R is hydrogen, hydroxyl, or an organic group of 1 to 70 carbon atoms, and n is an integer of 1 to 15; more preferably, R is hydrogen, hydroxyl, or an organic group of 1 to 40 carbon atoms, and n is an integer of 1 to 10.

The following compounds of formulae (5) to (12) may be taken as specific examples of the compound (A) of formula (1):

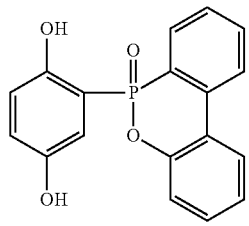
(5)

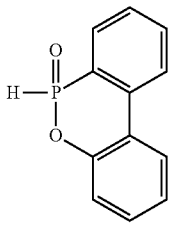
(5-1)

(5-2)

in formula (5), $R^{50}$ includes n formulae (5-1), m formula (5-2), n is an integer of 1 to 5, m is an integer of 1 to 5, n+m is 6; $R^2$ is hydrogen or methyl; and $R^3$ is hydrogen or methyl,

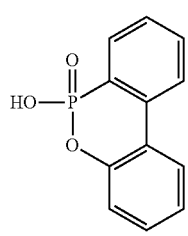
(6)

(7)

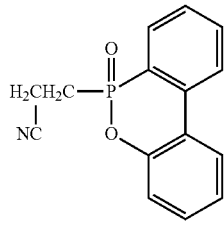
(8)

(9)

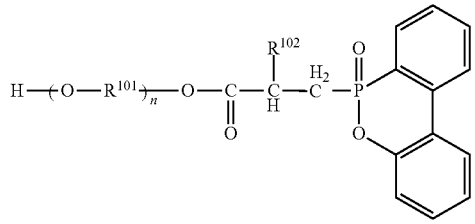
(10)

in formula (10), $R^{101}$ is alkylene having 2 to 12 carbon atoms may have a ring structure, $R^{102}$ is alkyl of 1 to 3 carbon atoms or hydrogen, and n is an integer of 1 to 30,

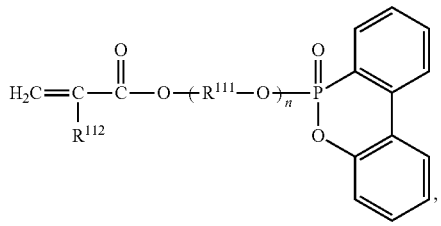
(11)

in formula (11), $R^{111}$ is alkylene having 2 to 12 carbon atoms may have a ring structure, $R^{112}$ is alkyl of 1 to 3 carbon atoms or hydrogen, and n is an integer of 1 to 30,

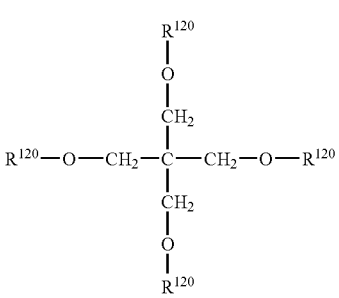
(12)

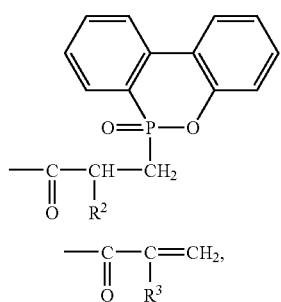

(12-1)

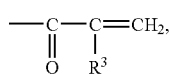

(12-2)

in formula (12), $R^{120}$ includes n formulae (12-1), m formulae (12-2), n is an integer of 1 to 3, m is an integer of 1 to 3, and n+m is 4; $R^2$ is hydrogen or methyl; and $R^3$ is hydrogen or methyl.

Among these Compounds, the compound of formula (5) is desirable for Compound (A), since the cured film formed thereby has a higher strength.

1.2 Polymerizable Monomer (B) of the Invention

As long as the polymerizable monomer (B) contained in the ink-jet ink of the invention is a polymerizable compound having a free radical, the polymerizable monomer (B) is not specially limited. As for the polymerizable monomer (B), a polymerizable monomer having a hydroxyl is preferable, that is because of higher adhesion to the substrate of the obtained cured film. As for the polymerizable monomer having a hydroxyl, a monofunctional monomer is more preferable, that is because the ink-jet ink has a desirable jetting property as an essential characteristic of the ink-jet ink, which thus is more preferred.

The monofunctional monomer having a hydroxyl preferably has a structure of formula (2):

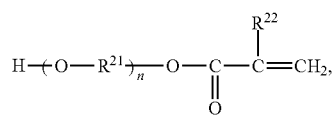

(2)

wherein $R^{21}$ is alkylene having 2 to 12 carbon atoms may have a ring structure, $R^{22}$ is alkyl of 1 to 3 carbon atoms or hydrogen, and n is an integer of 1 to 30.

As for the compound of formula (2), preferably, $R^{21}$ is alkylene having 2 to 12 carbon atoms may have a ring structure, $R^{22}$ is methyl or hydrogen, and n is an integer of 1 to 10. More preferably, $R^{21}$ is alkylene having 2 to 12 carbon atoms may have a ring structure, $R^2$ is methyl or hydrogen, and n is an integer of 1 to 5.

The following compounds may serve as examples of the above compound: 2-hydroxyethyl(meth)acrylate, 2-hydroxypropyl(meth)acrylate, 4-hydroxybutyl (meth)acrylate, 1,4-cyclohexanedimethanol mono(meth)acrylate, and N-hydroxyethyl methacrylamide, etc.

Besides the monofunctional monomer having a hydroxyl, a polymerizable monomer may also be used as the polymerizable monomer (B) of the invention. The following compounds may be taken as examples of such polymerizable monomer (B): multifunctional polymerizable monomer having a hydroxyl, monofunctional polymerizable monomer having no hydroxyl, and multifunctional polymerizable monomer having no hydroxyl.

The following compounds may serve as specific examples of the multifunctional polymerizable monomer having a hydroxyl: di(meth)acrylate modified by ethylene oxide isocyanurate, pentaerythritol di(meth)acrylate, pentaerythritol di(meth)acrylate monostearate, pentaerythritol tri(meth)acrylate, trimethylolpropane di(meth)acrylate, dipentaerythritol di(meth)acrylate, dipentaerythritol tri(meth)acrylate, dipentaerythritol tetra(meth)acrylate, and dipentaerythritol penta(meth)acrylate, etc. The cured film formed by di(meth)acrylate modified by ethylene oxide isocyanurate has a high heat resistance, and thus di(meth)acrylate modified by ethylene oxide isocyanurate is preferred.

The following compounds may serve as specific examples of the monofunctional polymerizable monomer having no hydroxyl: glycidyl(meth)acrylate, 3,4-epoxycyclohexyl (meth)acrylate, methylglycidyl(meth)acrylate, 3-methyl-3-(meth)acryloxy methyloxetane, 3-ethyl-3-(meth)acryloxy methyloxetane, 3-methyl-3-(meth)acryloxy ethyloxetane, 3-ethyl-3-(meth)acryloxy ethyloxetane, p-vinylphenyl-3-ethyl oxetan-3-ylmethyl ether, 2-phenyl-3-(meth)acryloxy methyloxetane, 2-trifluoromethyl-3-(meth)acryloxy methyloxetane, 4-trifluoromethyl-2-(meth)acryloxy methyloxetane, (meth)acrylic acid, methyl (meth)acrylate, ethyl(meth)acrylate, isopropyl(meth)acrylate, butyl(meth)acrylate, isobutyl(meth)acrylate, t-butyl(meth)acrylate, cyclohexyl (meth)acrylate, benzyl (meth)acrylate, styrene, methylstyrene, chloromethylstyrene, (3-ethyl-3-oxetane)methyl (meth)acrylate, N-cyclohexyl maleimide, N-phenyl maleimide, vinyltoluene, tricyclo[5.2.1.0$^{2,6}$]decanyl(meth)acrylate, dicyclopentenyloxyethyl(meth)acrylate, isobornyl(meth)acrylate, phenyl(meth)acrylate, glycerol mono(meth)acrylate, polystyrene macromonomer, polymethyl methacrylate macromonomer, 5-tetrahydrofurfuryloxycarbonylpentyl (meth)acrylate, (meth)acrylate of ethylene oxide adduct of lauryl alcohol, crotonic acid, α-chloroacrylic acid, cinnamic acid, maleic acid, fumaric acid, itaconic acid, citraconic acid, mesaconic acid, ω-carboxyl polycaprolactone mono(meth) acrylate, mono[2-(meth)acryloxy ethyl]succinate, mono[2-(meth)acryloxy ethyl]maleate, mono[2-(meth)acryloxy ethyl]cyclohexylene-3,4-bicarbonate, (meth)acrylamide, N,N-dimethyl(meth)acrylamide, N,N-diethyl(meth)acrylamide, N,N-dimethylamine propyl(meth)acrylamide, N-isopropyl(meth)acrylamide, N-acryloyl morpholine, N-phenyl maleimide, N-cyclohexyl maleimide, etc.

The following compounds may serve as examples of the multifunctional polymerizable monomer having no hydroxyl: bisphenol F ethylene oxide modified diacrylate, bisphenol A ethylene oxide modified diacrylate, polyethylene glycol diacrylate, polypropylene glycol diacrylate, 1,4-butanediol diacrylate, 1,6-hexanediol diacrylate, 1,9-nonanediol diacrylate, 1,4-cyclohexane dimethanol diacrylate, 2-n-butyl-2-ethyl-1,3-propylene glycol diacrylate, trimethylolpropane tri(meth)acrylate, ethylene oxide modified trimethylolpropane tri(meth)acrylate, propylene oxide modified trimethylolpropane tri(meth)acrylate, epichlorohydrin modified trimethylolpropane tri(meth)acrylate, di-(trimethylolpropane) tetra(meth)acrylate, glycerol tri(meth)acrylate, epichlorohydrin modified glycerol tri(meth)acrylate, diglycerol tetra(meth)acrylate, pentaerythritol tetra(meth)acrylate, dipentaerythritol hexa(meth)acrylate, caprolactone modified dipentaerythritol hexa(meth)acrylate, ethylene oxide modified phosphate tri(meth)acrylate, tris[(meth)acryloxy ethyl]isocyanuric acid, caprolactone modified tris[(meth)acryloxy ethyl]isocyanuric acid, urethane (meth)acrylate, and etc.

The polymerizable monomer (B) used in the invention may be a compound or a mixture of two or more different compounds. For example, the polymerizable monomer (B) used in the invention may be a mixture of a polymerizable monomer having a hydroxyl and other polymerizable monomers.

If the ink-jet ink of the invention contains both a monofunctional polymerizable monomer having a hydroxyl and a multifunctional (meth)acrylate as the polymerizable monomer (B), the ink has a high sensitivity to ultraviolet (UV) lights, and the cured film formed by curing the ink is quite flexible, which is preferred.

In the ink-jet ink of the invention, the content of the polymerizable monomer (B) is preferably 5 wt %-90 wt % based on the total weight except the ink-jet ink solvent (the solid content), and thus, the formed cured film has a desirable balance in terms of sensitivity to UV lights, jetting property, and heat resistance.

The content of the multifunctional (meth)acrylate serving as the polymerizable monomer (B) is preferably 20 wt %-80 wt % based on the whole weight of the polymerizable monomer (B), and thus achieving a desirable balance between high sensitivity and flexibility.

1.3 Photo-Polymerization Initiator (C)

As long as the photo-polymerization initiator (C) contained in the ink-jet ink of the invention is a compound capable of generating free radicals upon being irradiated by UV lights or visible lights, the photo-polymerization initiator (C) of the invention is not specially limited. The following compounds may serve as examples of the photo-polymerization initiator (C): the compound of formula (3), the compound of formula (4), benzophenone, Michler's ketone, 4,4'-bis(diethylamino)benzophenone, xanthone, thioxanthone, isopropylxanthone, 2,4-diethylthioxanthone, 2-ethylanthraquinone, acetophenone, 2-hydroxyl-2-methylpropiophenone, 2-hydroxyl-2-methyl-4'-isopropylpropiophenone, 1-hydroxyl cyclohexylphenylketone, benzoin isopropyl ether, benzoin isobutyl ether, 2,2-diethoxyacetophenone, 2,2-dimethoxy-2-phenylacetophenone, camphorquinone, benzanthraquinone, 2-methyl-1-[4-(methylthio)phenyl]-2-morpholinylpropan-1-one, 2-benzyl-2-dimethylamino-1-(4-morpholinylphenyl)-butanone-1, ethyl 4-dimethylaminobenzoate, isoamyl 4-dimethylaminobenzoate, 4,4'-di-(t-butylperoxycarbonyl)benzophenone, 3,4,4'-tri(t-butylperoxycarbonyl)benzophenone, 2-(4'-methoxystyrenyl)-4,6-bis(trichloromethyl)-s-triazine, 2-(3',4'-dimethoxystyrenyl)-4,6-bis(trichloromethyl)-s-triazine, 2-(2',4'-dimethoxystyrenyl)-4,6-bis(trichloromethyl)-s-triazine, 2-(2'-methoxystyrenyl)-4,6-bis(trichloromethyl)-s-triazine, 2-(4'-pentyloxystyrenyl)-4,6-bis(trichloromethyl)-s-triazine, 4-[p-N,N-di-(ethoxycarbonylmethyl)]-2,6-di-(trichloromethyl)-s-triazine, 1,3-bis(trichloromethyl)-5-(2'-chlorophenyl)-s-triazine, 1,3-bis(trichloromethyl)-5-(4'-methoxyphenyl)-s-triazine, 2-(p-dimethylaminostyrenyl)benzoxazole, 2-(p-dimethylaminostyrenyl)benzothiazole, 2-mercaptobenzothiazole, 3,3'-carbonylbis(7-diethylaminocoumarin), 2-(o-chlorophenyl)-4,4',5,5'-tetraphenyl-1,2'-biimidazole, 2,2'-bis(2-chlorophenyl)-4,4',5,5'-tetrakis(4-ethoxycarbonylphenyl)-1,2'-biimidazole, 2,2'-bis(2,4-dichlorophenyl)-4,4',5,5'-tetraphenyl-1,2'-biimidazole, 2,2'-bis(2,4-dibromophenyl)-4,4',5,5'-tetraphenyl-1,2'-biimidazole, 2,2'-bis(2,4,6-trichlorophenyl)-4,4',5,5'-tetraphenyl-1,2'-biimidazole, 3-(2-methyl-2-dimethylaminopropionyl)carbazole, 3,6-bis(2-methyl-2-morpholinylpropionyl)-9-n-dodecylcarbazole, 1-hydroxyl cyclohexylphenylketone, bis($\eta^5$-2,4-cyclopentadien-1-yl)-bis(2,6-difluoro-3-(1H-pyrrol-1-yl)-phenyl)titanium, and etc. The compound of formula (3) or the compound of formula (4) is preferred, since the formed cured film has relatively high flame retardancy.

The photo-polymerization initiator (C) used in the invention may be a compound or a mixture of two or more different compounds.

The content of the photo-polymerization initiator (C) used in the invention is preferably 1 weight part to 50 weight parts based on 100 weight parts of the polymerizable monomer (B); thus, the ink-jet ink of the invention has a higher sensitivity. In addition, the content of the photo-polymerization initiator (C) is preferably 3 weight parts to 40 weight parts based on 100 weight parts of the polymerizable monomer (B); thus the cured film formed by the inkjet ink of the invention has a higher flexibility.

1.4 Other Components

In order to improve the jetting property, the storage stability of the ink or the durability of the formed cured film, the ink-jet ink of the invention contains a solvent, a polymerization inhibitor, an alkali-soluble polymer, epoxy resin, colorant, and so on. These components may be a compound or a mixture of two or more different compounds.

1.4.1 Solvent

The ink-jet ink of the invention may contain a solvent capable of improving the jetting property of the ink. The solvent contained in the ink-jet ink of the invention preferably has a boiling point of greater than or equal to 100° C.

The following compounds may serve as examples of the solvent with a boiling point greater than or equal to 100° C.: water, butyl acetate, butyl propionate, ethyl lactate, methyl oxyacetate, ethyl oxyacetate, butyl oxyacetate, methyl methoxyacetate, ethyl methoxyacetate, butyl methoxyacetate, methyl ethoxyacetate, ethyl ethoxyacetate, methyl 3-oxypropionate, ethyl 3-oxypropionate, methyl 3-methoxypropionate, ethyl 3-methoxypropionate, methyl 3-ethoxypropionate, ethyl 3-ethoxypropionate, methyl 2-oxypropionate, ethyl 2-oxypropionate, propyl 2-oxypropionate, methyl 2-methoxypropionate, ethyl 2-methoxypropionate, propyl 2-methoxypropionate, methyl 2-ethoxypropionate, ethyl 2-ethoxypropionate, methyl 2-oxy-2-methylpropionate, ethyl 2-oxy-2-methylpropionate, methyl 2-methoxy-2-methylpropionate, ethyl 2-ethoxy-2-methylpropionate, methyl pyruvate, ethyl pyruvate, propyl pyruvate, methyl acetoacetate, ethyl acetoacetate, methyl 2-oxobutyrate, ethyl 2-oxobutyrate, dioxane, ethylene glycol, diethylene glycol, triethylene glycol, propylene glycol, dipropylene glycol, tripropylene glycol, 1,4-butanediol, ethylene glycolmonoisopropyl ether, ethylene glycolmonobutyl ether, propylene glycol monomethyl ether, propylene glycol monomethyl ether acetate, propylene glycol monoethyl ether acetate, propylene glycol monopropyl ether acetate, dipropylene glycol monoethyl ether acetate, dipropylene glycol monobutyl ether acetate, ethylene glycol monobutyl ether acetate, cyclohexanone, cyclopentanone, diethylene glycol monomethyl ether, diethylene glycol monomethyl ether acetate, diethylene glycol monoethyl ether, diethylene glycol monoethyl ether acetate, diethylene glycol monobutyl ether, diethylene glycol monobutyl ether acetate, diethylene glycol dimethyl ether, diethylene glycol diethyl ether, diethylene glycol methylethyl ether, toluene, xylene, anisole, γ-butyrolatone, N,N-dimethylacetamide, N-methyl-2-pyrrolidone, dimethylimidazolidone, and etc.

Among those solvents, dipropylene glycol monoethyl ether acetate, dipropylene glycol monobutyl ether acetate, propylene glycol monomethyl ether acetate, propylene glycol monoethyl ether acetate, methyl 3-methoxypropionate, ethyl 3-ethoxypropionate, diethylene glycol monoethyl ether acetate, diethylene glycol monobutyl ether acetate, diethylene glycol dimethyl ether, diethylene glycol methylethyl ether are preferred, since the jetting of the ink can be stable.

The solvent may be a compound or a mixture of two or more different compounds.

In the ink-jet ink of the invention, the concentration of the solid contents in the solvent is preferably not less than or equal to 20 wt %.

1.4.2 Polymerization Inhibitor

In the ink-jet ink of the invention, a polymerization inhibitor may also be used for improving the storage stability.

The following compounds may serve as examples of the polymerization inhibitor: 4-methoxyphenol, hydroquinone, phenothiazine, and etc. Among those polymerization inhibitors, phenothiazine is preferred to serve as the polymerization inhibitor considering a small variation in viscosity of the ink when the inkjet head is heated during the jetting process.

The polymerization inhibitor may be a compound or a mixture of two or more different compounds.

In order to meet the requirements in both storage stability and high sensitivity of the ink, the content of the added polymerization inhibitor is preferably about 0.001 weight parts to 1 weight parts based on 100 weight parts of the polymerizable monomer (B).

1.4.3 Alkali-Soluble Polymer

The ink-jet ink of the invention may contain an alkali-soluble polymer.

The ink-jet ink containing an alkali-soluble polymer may be used in a process of, for example, firstly patterning by using the inkjet, then processing the other parts except the pattern through etching, and then stripping the pattern with an alkali (etching resist).

As long as 0.1 g or more than 0.1 g of the alkali-soluble polymer used in the invention can be dissolved in 100 g aqueous solution of NaOH 5 wt % (50° C.), the alkali-soluble polymer is not specially limited. A polymer of a polymerizable monomer having a free radical and a carboxyl group, or a copolymer of a polymerizable monomer having a free radical and a carboxyl group with other polymerizable monomers having a free radical is preferred.

The following compounds may be taken as examples of the alkali-soluble polymer: opened-ring substances of benzyl methacrylate/methacrylate copolymer, benzyl methacrylate/2-hydroxyethyl methacrylate/methacrylate copolymer, benzyl methacrylate/5-tetrahydrofurfuryloxycarbonylpentyl (meth)acrylate/2-hydroxyethyl methacrylate/methacrylate copolymer, styrene/maleic anhydride copolymer, and so on. Among those compounds, benzyl methacrylate/5-tetrahydrofurfuryloxycarbonylpentyl (meth)acrylate/2-hydroxyethyl methacrylate/methacrylate copolymer is preferred, since the cured film formed by the ink containing such compound has a high acid resistance and can be easily removed by an alkali solution; and thus, the ink-jet ink can be preferably used to resist etching during the manufacturing of electronic circuit substrates.

In order to enable the cured film formed by the ink to have a high acid resistance and capable of being removed by an alkali solution, the ink-jet ink of the invention preferably contains about 10 weight parts to 100 weight parts alkali-soluble polymer based on 100 weight parts of the polymerizable monomer (B).

1.4.4 Epoxy Resin

The ink-jet ink of the invention may further contain an epoxy resin. If the ink-jet ink contains an epoxy resin, the durability of the cured film formed by curing the ink may be enhanced, which thus is preferred.

As long as the epoxy resin used in the invention has an oxiranyl group, it is not specially limited, and it preferably has two or more oxiranyl groups.

The following resins may serve as specific examples of the epoxy resin used in the invention: bisphenol A epoxy resin, glycidyl epoxy resin, alicyclic epoxy resin, and so on. As specific examples of such epoxy resins, the following products are exemplified: the products with Trade Name of Epikote 807, Epikote 815, Epikote 825, Epikote 827, Epikote 828, Epikote 190P, Epikote 191P (manufactured by Yuka-Shell Epoxy Co., Ltd); the products with Trade Name of Epikote 1004, Epikote 1256 (manufactured by Japan Epoxy Resins Co., Ltd); the products with Trade Name of Araldite CY177, Araldite CY184 (manufactured by Japan Ciba-geigy Co., Ltd); the products with Trade Name of Celloxide 2021P, EHPE-3150 (manufactured by Daicel Chemical Industries Co., Ltd); the products with Trade Name of Techmore VG3101L (manufactured by Mitsui Chemicals Co., Ltd), and etc.

In order to improve the durability of the cured film formed by curing the ink-jet ink of the invention, the ink-jet ink of the invention preferably contains the epoxy resin at a content of 1 weight part to 50 weight parts based on 100 weight parts of the polymerizable monomer (B).

1.4.5 Colorant

In order to easily distinguish the cured film formed by the ink-jet ink from the substrate when inspecting the state of the cured film, the ink-jet ink of the invention preferably contains the colorant at a content of about 1 weight part to 50 weight parts based on 100 weight parts of the polymerizable monomer (B).

Considering the heat resistance of the cured film formed by the ink-jet ink, the colorant is preferably pigment.

1.5 Preparation of the Ink-Jet Ink

The ink-jet ink of the invention is preferably prepared by filtering the solution formed by mixing essential ingredients. During filtering, a membrane filter made of fluorine resin, for example, may be used.

1.6 Viscosity of the Ink-Jet Ink

If the ink-jet ink of the invention has a viscosity of 3 mPa·s-300 mPa·s at 25° C., the ink has desirable jetting property, which thus is preferred. When the viscosity at 25° C. exceeds 20 mPa·s, if the ink-jet head is heated to decrease the viscosity during the jetting process, the ink may be jetted more stably.

1.7 Storage of the Ink-Jet Ink

If the ink-jet ink of the invention is stored at −20° C.-20° C., the viscosity has a small variation, and the storage stability is desirable.

2. Coating the Ink-Jet Ink Through the Ink-Jet Printing Process

The ink-jet ink of the invention can be used in a well-known ink-jet printing process that utilizes the ink for the coating process. The ink jet printing process includes, for example, applying mechanical energy on the ink and applying heat energy on the ink, so as to coat the ink. The ink-jet ink may be coated into a predetermined pattern through the ink jet printing process. In this way, the ink is merely coated on the parts where the ink is needed, thereby reducing the cost.

A coating unit used for coating the ink of the invention preferably has, for example, an ink-accommodating part and a coating head, and the coating unit may, for example, apply heat energy corresponding to a coating signal on the ink and thus generating ink drops due to the energy.

The coating head has, for example, a heat-generating part with a wetted surface containing metal and/or metal oxide.

The specific examples of the metal and/or metal oxide include, for example, Ta, Zr, Ti, Ni, Al and oxides thereof.

A coating device used for coating the ink of the invention preferably applies an energy corresponding to a coating signal on the ink in the cavity of the coating head of the ink-accommodating part and ink drops are generated due to the energy.

As for the above ink coating device, a coating device with the coating head and the ink-accommodating part being separated from each other may be used or a coating device with both the coating head and the ink-accommodating part integrally formed together may also be used. Alternatively, besides being separated from the coating head or integrally formed together with the coating head to be supported on a bracket, the ink-accommodating part may also be disposed at a fixed part of the device, and the ink is supplied to the coating head through an ink-supplying element, such as a tube.

3. Formation of the Cured Film

The cured film of the invention may be formed by firstly jetting the ink-jet ink of the invention onto the surface of the substrate through the well-known ink jet printing process, and then irradiating the ink by UV lights or visible lights. The ink irradiated by lights is cured by polymerizing with alkaline monomers into a three-dimensional cross-linked body, thus effectively inhibiting the diffusion of the ink. Therefore, high-precise patterns can be formed through using the ink-jet ink of the invention. The amount of UV irradiation is determined depending upon the composition of the ink-jet ink, and measured by the UV Intensity Meter UIT-201 equipped with a light sensor UVD-365PD (manufactured by Ushio INC. Co., Ltd), which is preferably 10 mJ/cm$^2$-1,000 mJ/cm$^2$.

Furthermore, if needed, the ink already jetted on the surface of the substrate and irradiated by lights may be further heated and baked, and preferably, heated at 120° C.-250° C. for 10-60 min.

In this specification, as long as the "substrate" acts as an object to be coated by the ink-jet ink of the invention, it is not specially limited, and the substrate is not limited to flat plate, but also may be curved plate.

Furthermore, the material of the substrate used in the invention is not specially limited, which may include, for example, polyester resin, such as polyethylene terephthalate (PET), polybutylene terephthalate (PBT); polyolefin resin, such as polystyrene, polypropylene; plastic films, such as polyvinyl chloride, fluorine resin, acrylic resin, polyamide, polycarbonate, polyimide; cellophane, acetate, metal foil, laminated film of polyimide and metal foil, transparent paper having filling effect, parchment paper or filling processing paper of polystyrene, clay binder, polyvinyl alcohol, starch, carboxymethyl cellulose (CMC), and glass, etc. The material for forming the substrate may further include additives, for example, pigment, dye, antioxidant, anti-aging agent, filler, UV absorber, antistatic agent, and/or electromagnetic inhibitor, without negatively influencing the invention.

The thickness of the substrate is not specially limited, but generally about 10 μm-2 mm, which may be appropriately adjusted according to the application purpose, preferably 15 μm-500 μm, and more preferably 20 μm-200 μm.

Depending upon the actual requirements, easy-bonding treatments such as corona treatment, plasma treatment, blasting treatment, may be performed on the surface of the substrate with the cured film formed thereon, or an easy-bonding layer is formed.

Hereinafter, the invention is further illustrated with reference to the following embodiments, but the invention is not limited thereto.

EXAMPLES

Synthesis Example 1

Synthesis of Compound (A)

At 90° C., 10.0 g of 4-hydroxybutyl acrylate (referred to as 4HBA hereinafter), 3.0 g of 9,10-dihydro-9-oxe-10-phosphaphenanthrene-10-oxide (referred to as HCA hereinafter), and 0.2 g of triphenyl phosphine were heated and stirred for 5 hr, to get a synthesis solution 1 with a rotational viscosity of 58 mPa·s at 25° C.

Example 1

According to the following composition, the synthesis solution 1, Ripoxy HF-DPHA30 (Trade Name, manufactured by Showa Highpolymer Co., Ltd, a mixture of the addition product of dipentaerythritol hexaacrylate and HCA (compound of formula (5)) and propylene glycol monomethyl ether acetate at a weight ratio of 80:20, referred to as HF-DPHA hereinafter), 4HBA as the monofunctional polymerizable monomer having a hydroxyl, 2,4,6-trimethylbenzoyl-diphenylphosphine oxide as the photo-polymerization initiator (manufactured by Ciba Specialty Chemicals Co., Ltd, DAROCUR (Trade Name) TPO, referred to as TPO), Techmore (Trade Name) VG3101L as the epoxy resin (manufactured by Mitsui Chemicals Co., Ltd, referred to as VG3101L), and phenothiazine as the polymerization inhibitor were mixed and dissolved, and then filtered by a 0.2 μm membrane filter made of fluorine resin, to formulate an ink-jet ink 1.

| | |
|---|---|
| Synthesis Solution 1 | 132.00 g |
| HF-DPHA | 45.00 g |
| 4HBA | 15.00 g |
| TPO | 5.00 g |
| VG3101L | 2.00 g |
| Phenothiazine | 0.02 g |

The ink-jet ink 1 was injected into an inkjet cartridge, and then the inkjet cartridge was installed in an ink-jet device DMP-2811 (Trade Name, manufactured by Dimatix Company), so as to print on Kapton (registered trademark, Trade Name, Du Pont-Toray Co., Ltd, Thick 150 μm, Type H, referred to as Kapton substrate hereinafter) as the polyimide film. The printing conditions were set as the line width of 200 μm, and the line interval of 200 μm. It was coated for once, the line length was 50 mm, the jetting speed from the nozzle was 10 times per second, and the jetting temperature was 60° C.

At 30 mJ/cm$^2$, the printed substrate was irradiated by UV lights with a wavelength of 365 nm, and then baked at 190° C. for 30 min to get a Kapton substrate 1 with lines and spaces patterns formed thereon. The substrate 1 was observed with a microscope to confirm that the lines had desirable linearity. Thus, the ink is confirmed to be suitable for coating on the substrate.

Secondly, the ink-jet ink 1 was coated on a template of 13 mm wide, 125 mm long, to become a thickness of 5 mm, and then it is irradiated by 365 nm UV lights at 30 mJ/cm$^2$ for 20 times, so as to be cured. Then, the template was removed, and the cured film was baked at 190° C. for 30 min. to get a sample 1 for burning test. The sample 1 for burning test was placed close to the flame of an igniter. Meanwhile, the sample 1 was burnt when contacting the flame, and was extinguished within about 1 second after getting away from the flame. Therefore, it can be confirmed that the ink-jet ink 1 has flame retardancy.

Comparative Example 1

According to the following composition, dipentaerythritol hexaacrylate (referred to as DPHA hereinafter), 4HBA as the monofunctional polymerizable monomer having a hydroxyl, TPO as the photo-polymerization initiator, VG3101L as the epoxy resin, and phenothiazine as the polymerization inhibitor were mixed and dissolved, and then filtered by a 0.2 μm membrane filter made of fluorine resin, to formulate an ink-jet ink 2.

| | |
|---|---|
| DPHA | 80.00 g |
| 4HBA | 110.00 g |
| TPO | 5.00 g |
| VG3101L | 2.00 g |
| Phenothiazine | 0.02 g |

The ink-jet ink 2 was coated, exposed, and baked through the same way as that in Example 1, to get a Kapton substrate 2. The substrate 2 was observed with a microscope to confirm that the lines had desirable linearity, and thus, the ink is confirmed to be suitable for being coating on the substrate.

Secondly, the ink-jet ink 2 is used to prepare a sample 2 for burning test through the same way as that in Example 1. The sample 2 for burning test was placed close to the flame of an igniter. The flames became large and the sample 2 was burnt once the sample 2 contacted the flames, and the sample 2 still keep burning even it got away from the flame. Therefore, it can be confirmed that the ink-jet ink 2 do not have flame retardancy.

The ink-jet ink of the invention may be applied in, for example, an etching resist or protective film used in electronic circuit substrates, a spacer or protective film of liquid crystal displays, an insulation film for flexible wiring boards, and electronic components using the same.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. An ink-jet ink, comprising a compound (A) of a formula (1), wherein R is an organic group having 1 to 100 carbon atoms and comprising a double bond, and n is an integer of 1 to 20:

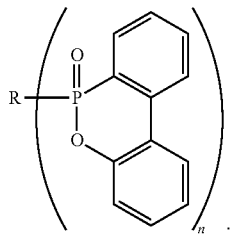

2. The ink-jet ink according to claim 1, wherein the double bond is a radical polymerizable double bond.
3. The ink-jet ink according to claim 1, wherein R comprises a hydroxyl group.
4. The ink-jet ink according to claim 1, wherein R comprises an oxiranyl group.
5. The ink-jet ink according to claim 1, wherein R comprises an oxetanyl group.
6. The ink-jet ink according to claim 1, wherein R comprises a carboxyl group.
7. The ink-jet ink according to claim 1, wherein R comprises an amino group.
8. The ink-jet ink according to claim 1, wherein the ink-jet ink further comprises a polymerizable monomer (B).
9. The ink-jet ink according to claim 8, wherein the polymerizable monomer (B) comprises a hydroxyl group.
10. The ink-jet ink according to claim 9, wherein the polymerizable monomer (B) comprises a monofunctional monomer having a hydroxyl group.
11. The ink-jet ink according to claim 10, wherein the polymerizable monomer (B) is a compound of a formula (2), wherein $R^{21}$ is alkylene having 2 to 12 carbon atoms and has a ring structure, $R^{22}$ is an alkyl group having 1 to 3 carbon atoms or hydrogen, and n is an integer of 1 to 30:

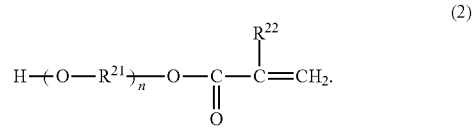

12. The ink-jet ink according to claim 11, wherein $R^{21}$ is alkylene having 2 to 12 carbon atoms and has a ring structure, $R^{22}$ is a methyl group or hydrogen, and n is an integer of 1 to 10.
13. The ink-jet ink according to claim 11, wherein $R^{21}$ is alkylene having 2 to 12 carbon atoms and has a ring structure, $R^{22}$ is a methyl group or hydrogen, and n is integer of 1 to 5.
14. The ink-jet ink according to claim 10, wherein the polymerizable monomer (B) comprises a multifunctional polymerizable monomer and a monofunctional monomer having a hydroxyl group.
15. The ink-jet ink according to claim 10, wherein the polymerizable monomer (B) is a compound of a formula (2), wherein $R^{21}$ is alkylene having 2 to 12 carbon atoms and does not have a ring structure, $R^{22}$ is an alkyl group having 1 to 3 carbon atoms or hydrogen, and n is an integer of 1 to 30:

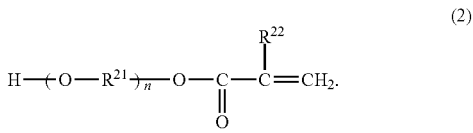

16. The ink-jet ink according to claim 15, wherein $R^{21}$ is alkylene having 2 to 12 carbon atoms and does not have a ring structure, $R^{22}$ is a methyl group or hydrogen, and n is an integer of 1 to 10.
17. The ink-jet ink according to claim 15, wherein $R^{21}$ is alkylene having 2 to 12 carbon atoms and does not have a ring structure, $R^{22}$ is a methyl group or hydrogen, and n is integer of 1 to 5.
18. The ink-jet ink according to claim 1, further comprising a photo-polymerization initiator (C).
19. The ink-jet ink according to claim 18, wherein the photo-polymerization initiator (C) is a compound of formula (3) or (4), wherein each of $R^1$-$R^{15}$ is independently hydrogen, an alkyl group having 1 to 5 carbon atoms, or a substituted phenyl group with a substituted group:

(3)

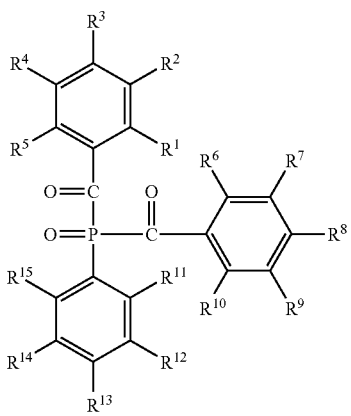

(4)

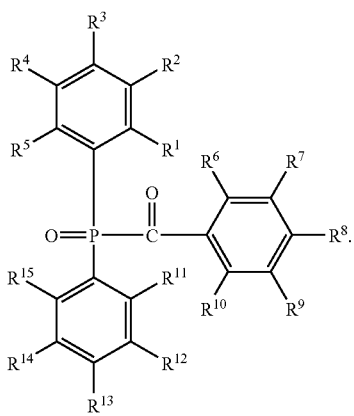

20. The ink-jet ink according to claim 19, wherein the photo-polymerization initiator (C) is one selected from the group consisting of bis(2,4,6-trimethylbenzoyl)phenyl phosphine oxide of formula (3) with $R^1$, $R^3$, $R^5$, $R^6$, $R^8$, and $R^{10}$ as a methyl group and $R^2$, $R^4$, $R^7$, $R^9$, $R^{11}$, $R^{12}$, $R^{13}$, $R^{14}$, and $R^{15}$ as hydrogen and (2,4,6-trimethylbenzoyl)diphenyl phosphine oxide of formula (4) with $R^6$, $R^8$, and $R^{10}$ as a methyl group and $R^1$, $R^2$, $R^3$, $R^4$, $R^5$, $R^7$, $R^8$, $R^{11}$, $R^{12}$, $R^{13}$, $R^{14}$, and $R^{15}$ as hydrogen.

21. The ink-jet ink according to claim 18, wherein the photo-polymerization initiator (C) is a compound of formula (3) or (4), wherein each of $R^1$-$R^{15}$ is independently hydrogen, an alkyl group having 1 to 5 carbon atoms, or a phenyl group without a substituent:

(3)

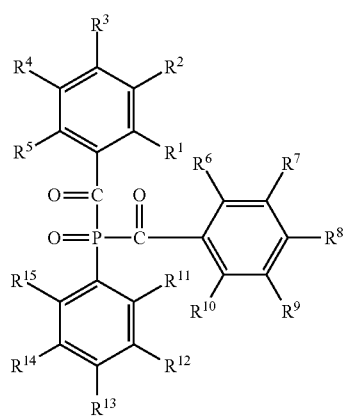

(4)

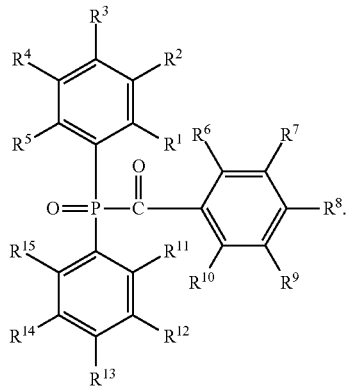

22. An ink-jet ink, comprising:

a compound (A), having a structure of formula (5), wherein the six $R^{50}$ groups of said formula (5) comprise a number "n" of formulae formula (5-1) and a number "m" of formula (5-2), n is an integer of 1 to 5, m is an integer of 1 to 5, and n+m is 6; $R^2$ is hydrogen or a methyl group, and $R^3$ is hydrogen or a methyl group:

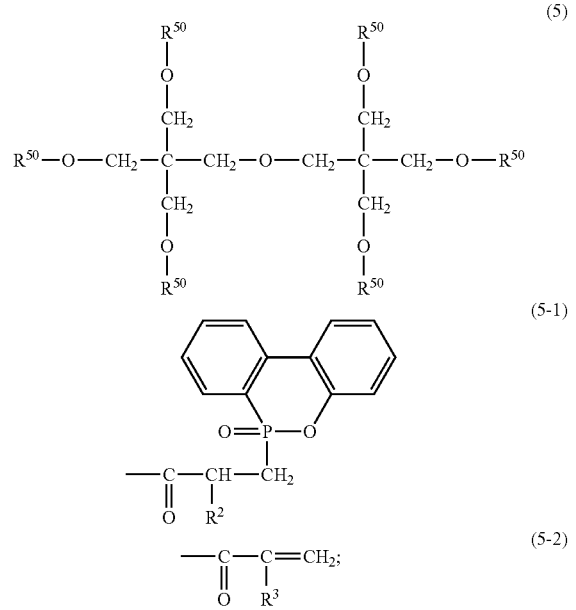

a polymerizable monomer (B), being one or more selected from the group consisting of 2-hydroxyethyl (meth)acrylate, 2-hydroxypropyl (meth)acrylate, 4-hydroxybutyl (meth)acrylate, and 1,4-cyclohexanedimethanol mono(meth)acrylate; and a photo-polymerization initiator (C), being one or more selected from the group consisting of bis (2,4,6-trimethylbenzoyl)phenyl phosphine oxide and (2,4,6-trimethylbenzoyl)diphenyl phosphine oxide.

* * * * *